United States Patent
Datta et al.

[11] Patent Number: 5,831,085
[45] Date of Patent: Nov. 3, 1998

[54] PROCESS FOR MANUFACTURE OF CEPHALOSPORIN SUCH AS CEFTAZIDIME AND INTERMEDIATE THEREOF

[75] Inventors: Debashish Datta; Bishwa Prakash Rai; Kishor Mehre, all of Madhya Pradesh, India

[73] Assignee: Lupin Laboratories Limited, Mumbai, India

[21] Appl. No.: 845,735

[22] Filed: Apr. 25, 1997

[30] Foreign Application Priority Data

Jan. 16, 1997 [IN] India ................. 22/MUM/97

[51] Int. Cl.$^6$ .................... C07D 501/46; C07D 277/587
[52] U.S. Cl. ............................ 540/225; 548/194
[58] Field of Search .................. 548/194; 540/225

[56] References Cited

U.S. PATENT DOCUMENTS

| | | | |
|---|---|---|---|
| 4,258,041 | 3/1981 | O'Callaghan et al. | 424/246 |
| 4,329,453 | 5/1982 | Brodie et al. | 424/246 |

FOREIGN PATENT DOCUMENTS

| | | |
|---|---|---|
| 0113568 | 7/1984 | European Pat. Off. |
| 0282531 | 9/1987 | European Pat. Off. |
| 0377987 | 7/1990 | European Pat. Off. |
| 2921316 | 12/1979 | Germany |
| 85/04659 | 10/1985 | WIPO |

*Primary Examiner*—Mark L. Berch
*Attorney, Agent, or Firm*—Merchant, Gould, Smith, Edell, Welter & Schmidt

[57] ABSTRACT

This invention relates to reactive derivative of 2-(2-amino-4-thiazolyl)-(Z)-2-[(1-tert butoxycarbonyl-l-methylethoxy)imino]acetic acid of the following formula I

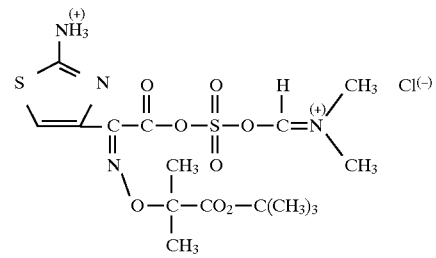

as well as to the use thereof in the manufacture of cephalosporin antibiotic such as ceftazidime of formula II.

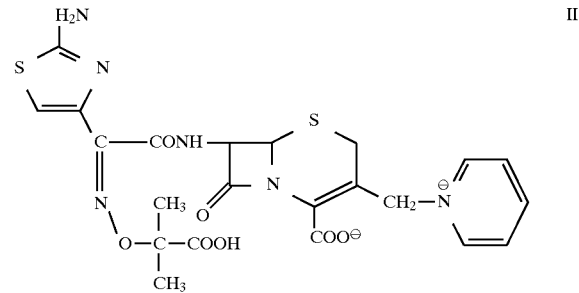

17 Claims, No Drawings

PROCESS FOR MANUFACTURE OF CEPHALOSPORIN SUCH AS CEFTAZIDIME AND INTERMEDIATE THEREOF

BACKGROUND OF THE INVENTION

FIELD OF THE INVENTION

This invention relates to reactive derivative of 2-(2-amino-4-thiazolyl)-(Z)-2-[(1-tert butoxycarbonyl-1-methylethoxy)imino]acetic acid of the following formula I

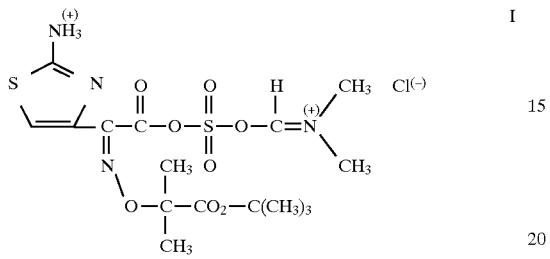

I

The present invention further relates to processes for the production of said reactive derivatives of formula I as well as to a process for the manufacture of cephalosporin antibiotic ceftazidime (II) using said reactive derivative of formula I.

DISCUSSION OF THE BACKGROUND

It is known that Ceftazidime [(6R, 7R)-7-[[2-amino-4-thiazolyl)-2-(1-carboxy-1-methylethoxy)imino]acetamido]-3-(1-pyridiniammethyl)-3-cephem-4carboxylic acid] of formula II is a broad-spectrum cephalosporin antibiotic described in U.S. Pat. No. 4,258,041 and ceftazidime (II) in its most stable pentahydrate form is described in U.S. Pat. No. 4,329,453.

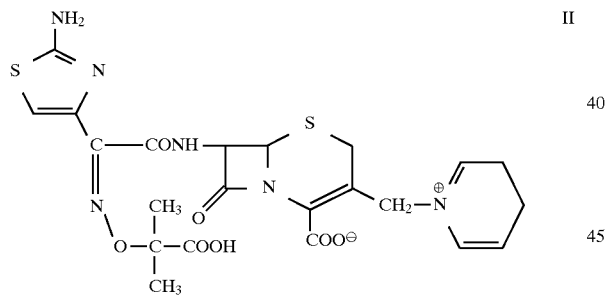

II

Numerous methods reported for the manufacture of cephalosporins including ceftazidime (II) basically utilise the chemistry involving N-acylation of 7-amino-3-subst-3-cephem-4-carboxylic acid with an activated derivative of 2-aminothiazole 2-oxyimino acetic acid.

The activated derivatives include an acid chloride, an acid anhydride, an activated ester and a mixed anhydried of 2-aminothiazolyl oximino acetic acid.

Alternatively, cephalosporins such as ceftazidime (II) can also be prepared by coupling an appropriate 2-aminothiazolyl oximino acetic acid in its free acid form with 7-amino-3-substd-3-cephem-4-carboxylic acid in the presence of condensing agent like N,N'-dicyclohexyl carbodiimide, N-ethyl-N-τ-dimethyl aminopropylcarbodiimide.

Such important methods reported in the prior art for the manufacture of ceftazidime (II) are described below:

1. U.S. Pat. No. 4,258,041 describes a process for the preparation of ceftazidime (II) which comprises N-acylation of (6R, 7R)-7-amino-3-(1-pyridiniummethyl)-3-cephem-4-carboxylic acid (III) with 2-(2-amino-4-thiazolyl)-(Z)-2-[(1-tert butoxycarbonyl-1-methylethoxy)imino]acetyl chloride (IV) in a mixture of N, N-dimethylacetamide (DMAC) and acetonitrile to provide the ceftazidime intermediate i.e. (6R, 7R)-7-[(Z)-2-(2-tritylaminothiazol-4-yl)-2-(2-tertbutoxycarbonyl-1-methyethoxyimino)acetamido]-3-(1-pyridiniummethyl)-3-cephem-4-carboxylic acid (V) which was purified by crystallization as a DMF solvate followed by deprotection with formic acid to yield ceftazidime (II). The process is schematically illustrated as follows:

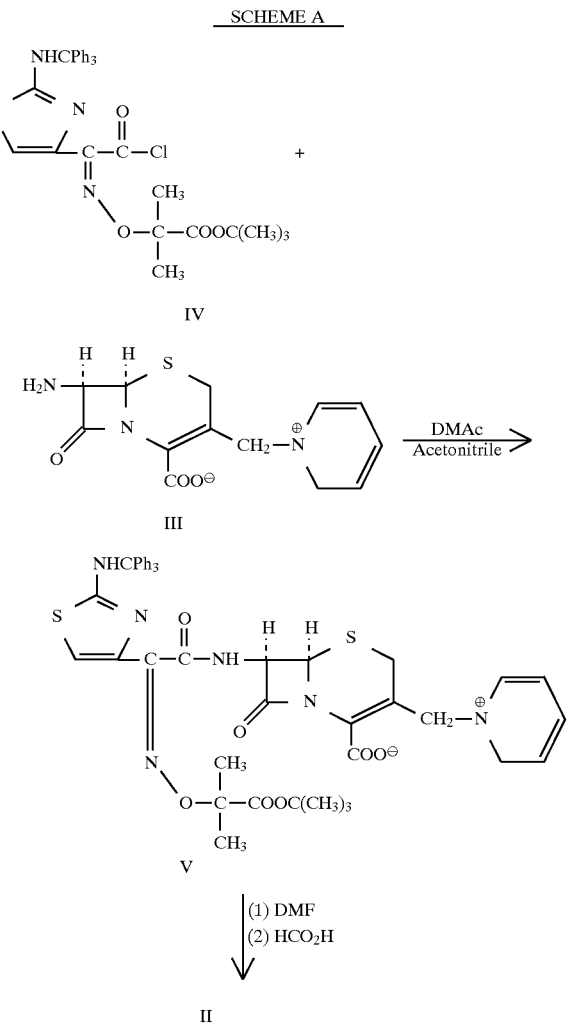

SCHEME A

The main disadvantage of this process is the protection and deprotection of the amino group of the thiazolyl ring which substantially lowers the yield of the final product. Another disadvantage is the use of the reactive derivative in the form of the acid chloride which is unstable in nature.

2. EP 113 568 describes a method for the preparation of ceftazidime (II) which is an improvement over the above method. The basic chemistry utilised in this process is same as above, however, the intermediate is directly crystallized out from the reaction mixture as a DM Ac solvate.

3. EP 377 987 disclosed a method similar to above two methods involving protection and deprotection of the amino group of the thiazolyl ring. The only difference is the use of mixed anhydride of 2-(2-tritylaminothiazol-4-yl)-2-(2-t-butyloxycarbonyl-1-methyethoxy)imino acetic acid with an alkyl or aryl sulfonic acid or a phosphoric acid.

4. EP 282 531 describes a method for the preparation of a ceftazidime intermediate viz. ceftazidime tert butyl ester of formula VI wherein 7-amino-3-(1-pyridinium methyl)-3-cephem-4-carboxylate (III) is coupled with 2-(2-amino-4-thiazolyl)-(Z)-2-[(1-tertbutoxycarbonyl-methylethoxy)imino]thio acetic acid S-benzothiazolyl ester of formula VII to obtain ceftazidime tert butyl ester (VI).

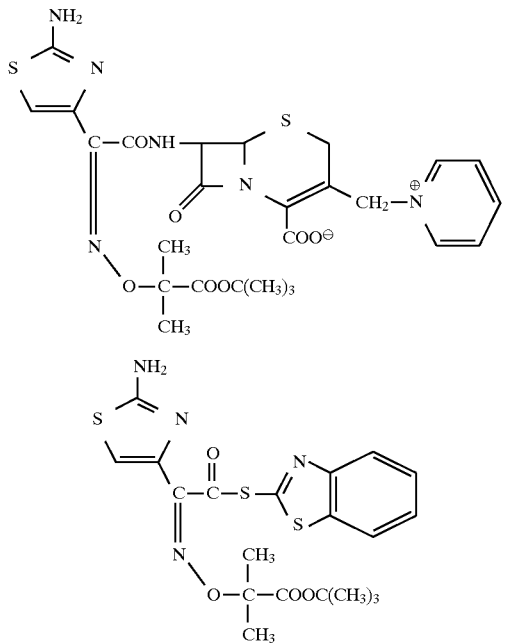

The preparation of 2-(2-amino-4-thiazolyl)-(Z)-2-[(1-tertbutoxycarbonyl-1 -methylethoxy)imino]thioacetic acid S-benzothiazolyl ester (TAEM)(VII) involves reaction of the corresponding acid with bis[benzothiazol-2-yl)disulfide and triphenyl phosphine.

In spite of the elegance of the chemistry employed, the use of costly reagents like triphenyl phosphine renders this process very costly. Moreover, an additional step is required to remove the by products resulting from the process.

5. WO 85/4659 utilises similar chemistry as above i.e. TAEM(VII) is used as the reactive derivative which is coupled with 7-amino-3-(1-pyridiniummethyl)-3-cephem- 4-carboxylate (III). However, in this process ceftazidime tert butyl ester (VI) is obtained only in an amorphous form which is difficult to isolate.

6. DE 2 921 316 describes a process for the manufacture of ceftazidime (II) wherein (6R, 7R)-3-acetoxymethyl-7-amino-3-cephem-4-carboxylate is reacted with an appropriate N-protected thiazole acetic acid in the presence of dicyclohexyl-carbodiimide in dimethylformamide to give an intermediate which was deblocked with trifluoroacetic acid followed by treatment with pyridine and sodium iodide to give ceftazidime sodium salt.

Thus this process also involves the protection and deprotection of the amino group of the thiazolyl ring of the conventional processes, resulting in lowering of the overall yield of the final product.

Moreover, the process also involves the use of dicyclohexyl carbodimide as a condensing agent which is toxic in nature.

Thus, it is evident from the description of the prior art that the processes involved in the manufacture of ceftazidime are costly, lengthy involving protection or deprotection of amino group or have other limitations such as the use of acid chloride of the corresponding 2-(2-aminothiazol-4-yl)-2-oxyimino acetic acid which is unstable in nature.

SUMMARY OF THE INVENTION

It is thus an object of the present invention to provide reactive derivatives of 2-(2-aminothiazol-4-yl)-2-(2-tertbutoxycarbonyl-1 -methylethoxy)iminoacetic acid of formula I which would be suitable for use in the manufacture of cephalosporin antibiotics ceftazidime (II).

Yet another object of the present invention is to provide for a process for the manufacture of said reactive derivative of formula I which would be practically viable and simple to carry out.

Yet another object of the present invention is to provide a simple process for the synthesis of cephalosporin antibiotic ceftazidime (II) without taking recourse to the protection and deprotection of the amino group of the thiazolyl ring as reported in the prior art.

A further object of the present invention is to provide a process for the synthesis of cephalosporin antibiotic ceftazidime (II) which may be more simply carried out and more cost effective than known methods.

Other objects of the invention will be apparent from the description of the invention provided hereunder.

Thus, according to one aspect of the present invention compound of formula I

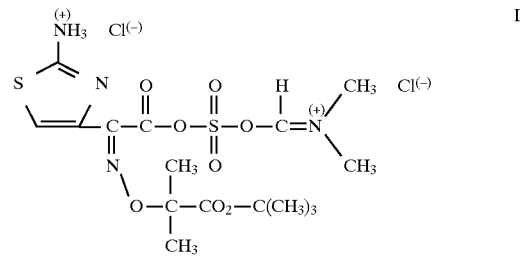

is provided by a process comprising reacting dimethyl formiminium chloride chlorosulphate (DFCCS) of formula (IX)

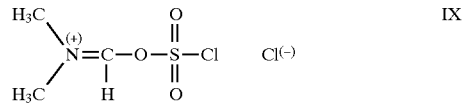

with (Z)-2-(2-aminothiazol-4-yl)-2-[(1 -tertbutoxycarbonyl-1-methylethoxy)imino]acetic acid (VIII) in a solvent such as dichloromethane at a temperature ranging from −20° C. to 25° C. to yield the compound of formula I.

In particular in accordance with the present invention the reactive derivative of 2-(2-amino-4-thiazolyl)-(Z)-2-[1-tert butoxy-carbonyl-1-methylethoxy) imino]acetic acid of formula I is obtained by a process comprising activating (Z)-2-(2-aminothiazol-4-yl)-2-[(1-tertbutoxycarbonyl-1-methylethoxy) imino]acetic acid (VIII)

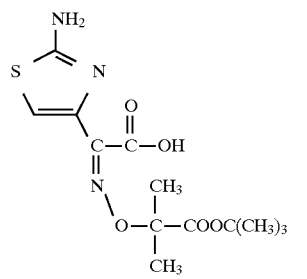

with N,N-dimethylformiminium chloride chlorosulfate (DFCCS) (IX)

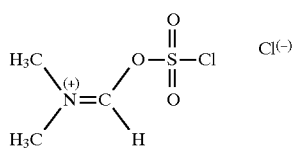

in dichloromethane at a temperature ranging from −20° C. to −25° C. to provide the reactive derivative of formula I.

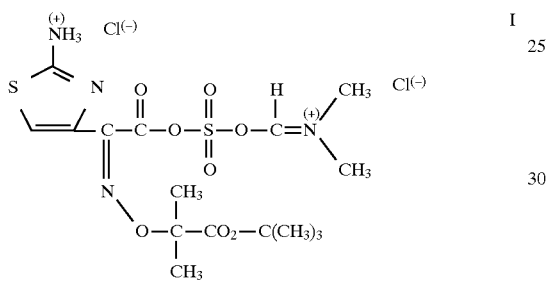

During the above process of manufacture of the reactive derivative of formula I and in particular during the said activation of 2-[(2-aminothiazol-4-yl)-2-(1-tertbutoxycarbonyl-1-methylethoxy)imino]acetic acid (VIII), the molar ratio of DFCCS (IX)

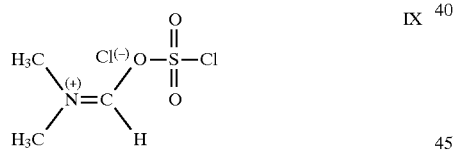

to said thiazolyl acetic acid (VIII) was preferably maintained in the range of 1.0 to 1.3.

In accordance with a further aspect of the present invention there is provided a process for the manufacture of the cephalosporin antibiotic ceftazidime of formula II

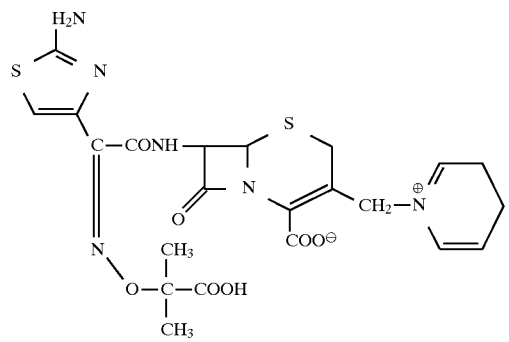

comprising
a) silylating 7-amino-3-(1-pyridiniummethyl)-3-cephem-4-carboxylic acid of formula III

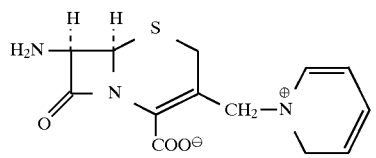

with a silylating agent in the presence of an acid scavenging agent at a temperature ranging for 18° C. to 25° C. to provide silylated 7-amino-3-(1-pyridiniummethyl)-3-cephem-4-carboxylic acid of formula (X)

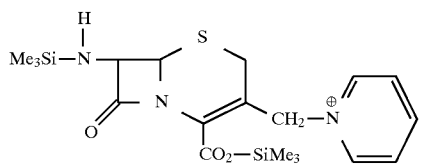

b) activating (Z)-2-(2-aminothiazol-4-yl)-2-[(1-tertbutoxycarbonyl-1-methylethoxy)imino]acetic acid (VIII)

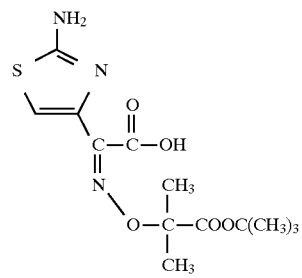

with N,N-dimethylformiminium chloride chlorosulfate (DFCCS) (IX)

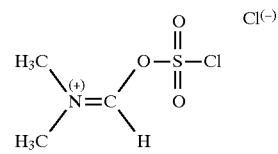

in dichloromethane at a temperature ranging from −20° C. to −25° C. to obtain the reactive derivative of formula I:

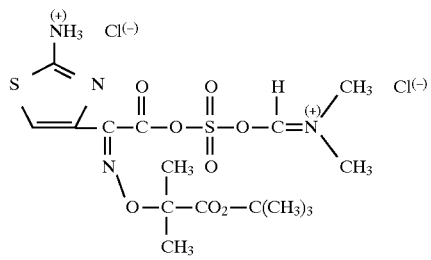

c) acylating the silylated 7-amino-3-(1-pyridiniummethyl)-3-cephem-4-carboxylic acid (X) of step (a) with the reactive derivative of formula I of step (b) at a temperature ranging from −70° C. to −60° C., preferably −70° C. to −65° C. to obtain ceftazidime tertbutyl ester (VI),

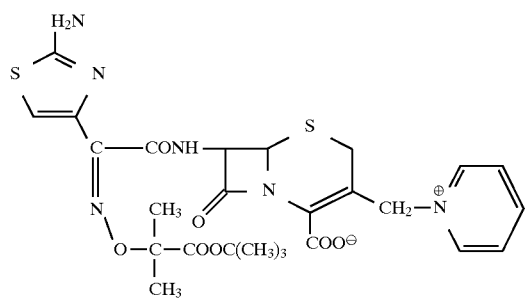

VI

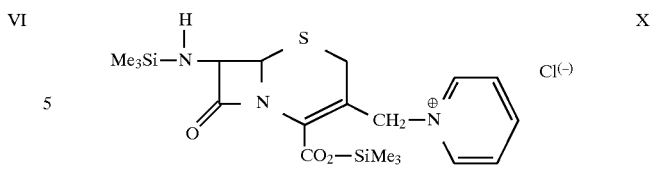

X which is converted to ceftazidime pentahydrate (II) via ceftazidime dihydrochloride.

DETAILED DESCRIPTION OF THE INVENTION

The above disclosed process of the invention utilizes a reactive derivative of formula I which is obtained by reacting 2-(2-aminothiazol-4-yl)-2-(1-tertbutoxy carbonyl-1-methylethoxy)imino acetic acid of formula IX with dimethyl formiminium chloride chlorosulfate (DFCCS) of formula VIII in a solvent such as dichloromethane at a temperature ranging from $-20°$ C. to $-25°$ C.

DFCCS (IX) is a known compound and described in the literature vis. Z. Chem, 6(4), 148 (1966), J. C. S. Perkin Trans I, 2004–2007 (1972); Bull Chem Soc Jpn, 58, 1063–1064; Adv.-Org. Chem. 9(2), 5, (1979); Synthetic Reagents Vol. 4, 388–389; Angew Chem International Edit, 1 (12), 647 (1962).

The method for the preparation of DFCCS (IX) from N,N-dimethylformamide and sulfuryl chloride, is described in our copending U.S. application Ser. No. 08/624,737 dated 26th Mar. 1996. The characteristics of DFCCS (IX) in comparison with DFCS a thionyl chloride-DMF adduct which is subject matter of another patent, are also described in the said U.S. application Ser. No. 08/624,737.

However, in the present invention it was observed that when the preparation of DFCCS (IX) was carried out in the presence of 0.5 to 0.7 volume of dichloromethane as the solvent, DFCCS (IX) of improved quality was obtained.

Thus, in the present invention DFCCS (IX) was prepared by reacting equimolar quantities of N,N-dimethylformamide and sulfuryl chloride in 0.5 volume of dichloromethane at $20°$ C.–$25°$ C. for 60–90 minutes.

During the activation of 2-[(2-aminothiazol-4-yl)-2-(1-tertbutoxycarbonyl-1-methylethoxy)imino]acetic acid (VIII), the molar ratio of DFCCS (IX) to said thiazolyl acetic acid (VIII) was preferably maintained in the range of 1.0 to 1.3.

Thus, the use of DFCCS (IX) for synthesis of the compound of formula I provides a practical, cost effective and safe method for manufacture of the desired cephalosporin antibiotic ceftazidime.

Thus the above process for the manufacture of ceftazidime (II) of the invention comprises reacting silylated 7-amino-3-(1-pyridiniummethyl)-3-cephem-4-carboxylic acid of formula X.

with reactive derivative of 2-(2-amino-thiazol-4-yl)-2-[(1-tertbutoxy carbonylmethylethoxy)imino]acetic acid of formula I in dichloromethane at a temperature ranging from $-60°$ C. to $-70°$ C. in the presence or absence of an acid scavenging agent to obtain ceftazidime tert butyl ester (VI), which was converted to ceftazidime dihydrochloride following known procedure such as described in U.S. Pat. No. 4,258,041, which is further converted to its most stable pentahydrate form by further known procedure such as described in U.S. Pat. No. 4,329,453.

During the acylation reaction an acid scavenging agent can be optionally used. The preferred acid scavenging agent is N,N-dimethyl aniline and preferably the acid scavenging agent should be added to the silylated 7-amino-3-(1-pyridiniummethyl)-3-cephem-4-carboxylic acid (X) at $-50°$ C.

The acylation reaction is carried out by maintaining the pH of the reaction mixture at 4.5 to 7.5. The pH is adjusted by addition of triethylamine.

During the process of the acylation reaction either the silylated 7-amino-3-(1-pyridiniummethyl)-3-cephem-4-carboxylic acid (X) can be added to the reactive derivative I or vice-versa. However, for better results the addition should be preferably completed within 5 to 15 minutes.

The process of the present invention for the manufacture of ceftazidime (II) is described in detail as follows:

In step I (Z)-2-(2-aminothiazol-4-yl)-2-[(1-tertbutoxycarbonyl-1-methylethoxy)imino]acetic acid (VIII) was activated with N,N-dimethylformiminium chloride chlorosulfate (IX) in 0.5 volume of dichloromethane at a temperature ranging from $-20°$ C. to $-25°$ C. The temperature of the resulting reaction mixture is raised to $-15°$ C.$\pm 2°$ C. to yield the reactive derivative of formula I.

In Step II 7-amino-3-(1-pyridiniummethyl)-3-cephem-4-carboxylic acid (III) was silylated with a silylating agent such as N,O-bis(trimethyl silyl)acetamide in dichloromethane in the presence of an acid scavenging agent such as N,N-dimethylaniline at a temperature ranging from $18°$ C. to $25°$ C.

In Step III the pre cooled reactive derivative of formula I is added to cooled silylated 7-amino-3-(1-pyridiniummethyl)-3-cephem-4-carboxylic acid (X) at a temperature ranging from $-70°$ C. to $-60°$ C. to yield ceftazidime tertbutyl ester (VI) which was further converted to ceftazidime pentahydrate by procedures disclosed in the prior art.

Ceftazidime tertbutyl ester (VI) was first converted to ceftazidime dihydrochloride by following the procedure disclosed in U.S. Pat. No. 4,258,041 which in turn was converted to the stable pentahydrate form of ceftazidime by the procedure disclosed in U.S. Pat No. 4,329,453.

The process of the present invention is illustrated in the following scheme B:

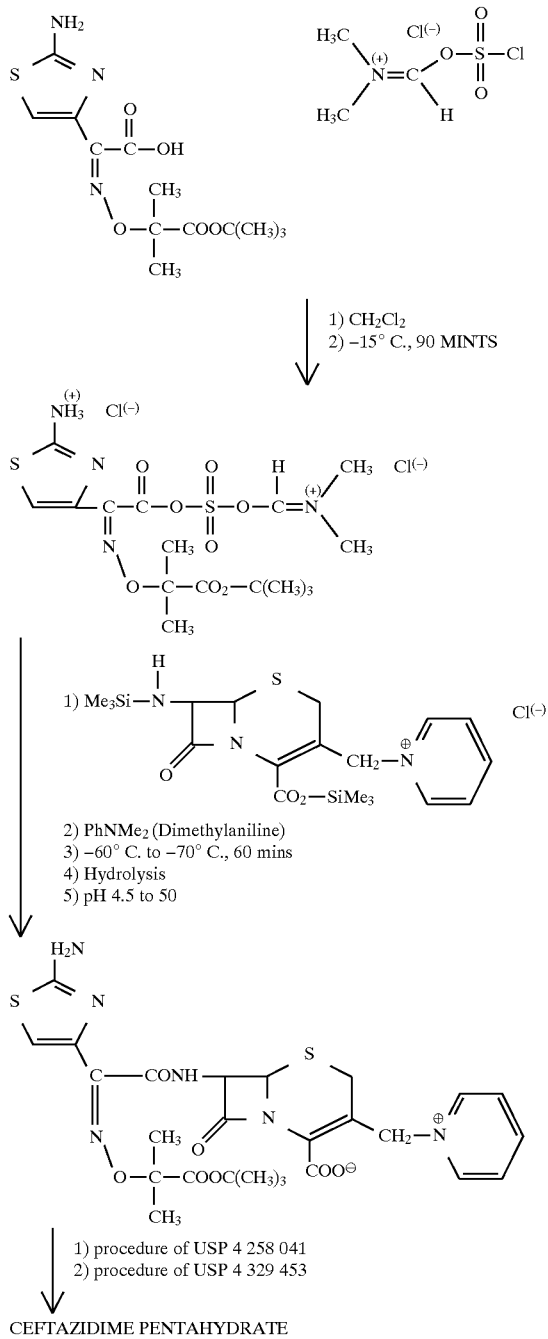

CEFTAZIDIME PENTAHYDRATE

SCHEME B

The silylation of 7-amino-3-(1-pyridiniummethyl)-3-cephem-4-carboxylic acid (III) is carried out by using conventional silylation agents such as N,O-bis(trimethylsilyl) acetamide, hexamethyldisilazane (HMDS). However, the preferred is N,O-bis(trimethylsilyl)acetamide, 4 moles of which is used per mole of the substrate.

The acid scavenging agent used during the silylation is selected from N,N-dimethylaniline, diethylamine, pyridine preferably N,N-dimethylaniline.

The acylation reaction is carried out at a temperature ranging from −70° C. to −60° C. preferably −70° C. to −65° C.

The present invention, its objects and advantages will be further apparent from the non limiting examples illustrated hereunder:

EXAMPLES

Example 1

Preparation of (6R, 7R)-7-[[(2-amino-4-thiazolyl)-2-(1-carboxy-1-methylethoxy)imino]acetamido]-3-(1-pyridiniummethyl)-3-cephem-4-carboxylate pentahydrate (ceftazidime pentahydrate).

I. Preparation (6R, 7R)-7-amino-3-(1-pyridiniummethyl)-3-cephem-4-carboxylic acid iodide monohydrate.

Iodine (117 g, 915 mmol) was taken in dichloromethane (750 ml) at room temperature and the temperature was further raised to 36° C. Hexamethyl disilazane (HMDS) 80 g, 496 mmol) was added to it as 35° C. over 30 hrs until the colour disappeared. Pyridine (90 g, 1168 mmol) was added to the reaction mixture in 60 minutes at 30° C. followed by addition of 7-aminocephalosporanic acid (50 g, 183 mmol) at 35° C. −40° C. The reaction was monitored by HPLC. The reaction mixture was cooled to 10° C. and isopropyl alcohol (220 ml) and water (30 ml) was added to it. The resulting reaction mixture was further cooled to 0° C. to 2° C. for 2 hours, filtered and the cake was washed with a mixture of isopropanol (80 ml) and water (5 ml), followed by acetone (100 ml).

The resulting product was taken in methanol (200 ml) at 10° C. and dissolved by adding 17% HCl, stirred for 60 minutes. The pH of the resulting solution was adjusted to 2.8 to 3.0 by addition of triethylamine. The resulting solution was cooled to 0° C. −5° C. for 60 minutes, filtered with a mixture of methanol and acetone (50:50) followed by chilled acetone (50 ml) and dried under vacuum at 35° C. for 2 hours to obtain 62 g (90%) of the product.

Water Content (KF): 3–4%

IR (KBr) cm$^{-1}$: 3300, 1790, 1600, 1480, 1400, 1140.

II. Preparation of (6R, 7R)-7-amino-(1-pyridiniummethyl)-3-cephem-4-carboxylic acid hydrochloride monohydrate.

The compound of Step I (1 g) was dissolved in 0.1N HCl (50 ml) at 20° C. The resulting product was precipitated by adding isopropanol (250 ml) at 20° C., filtered, washed with isopropanol (10 ml) and dried under vacuum for 2 hours at 40° C. to obtain 7.5 g of the product.

Water Content (KF): 4–5%

IR: (KBr) cm$^{-1}$: 3300, 1780, 1600

III. Preparation of (6R, 7R)-7-[(2-amino-4-thiazolyl)-2-[(I-tertbutoxy carbonyl-1-methylethoxy)imino]acetamido-3-(1-pyridiniummethyl)-3-cephem-4-carboxylate(ceftazidime tert butyl ester).

A) Silylation of (6R, 7R)-7-amino-3-(1-pyridiniummethyl)-3-cephem-4-carboxylic acid hydrochloride monohydrate.

(6R, 7R)-7-amino-3-(1-pyridiniummethyl)-3-cephem-4-carboxylic acid hydrochloride monohydrate (10 g, 26 mmoles) was taken in dichloromethane (100 ml) and then 40 ml of dichloromethane was distilled out. After cooling the reaction mixture to 25° C. , N,O-bis(trimethylsilyl) acetamide (21.2 g, 104 mmole) was added to it and agitated for 4 hours to get a clear solution. The reaction mixture was cooled to −70° C. and N,N-dimethylaniline (4.2 g, 34 mmol) was added to it.

B) Preparation of dimethyl formiminum chloride chlorosulfate (DFCCS) Sulfuryl chloride (4.761 g, 34 mmol) was taken in dichloromethane (5 ml) and the reaction mixture was cooled to −25° C. N,N-dimethylformamide (2.54 g, 34 mmole) was added to the reaction mixture slowly in 30 minutes and the temperature was raised to 22° C. and agitated for 90 minutes at the same temperature at which the oily layer separates out. Further, an additional 10 ml of dichloromethane was added to it and agitated for another 10 minutes. The oily layer containing DFCCS was separated out.

C) Activation of (Z)-2-(2-aminothiazol-4-yl)-2-[(1-tertbutoxy-carbonyl-1-methylethoxy)immino]acetic acid.

(Z)-2-(2-aminothiazol-4-yl)-2-[(1-tertbutoxycarbonyl-1-methylethoxy)imino]acetic acid (8.84 g, 26 mmol) was taken in dichloromethane (50 ml) and the resulting reaction mixture was cooled to -25° C. and the above oily layer containing DFCCS was added to it in 30 minutes. The temperature of the reaction mixture was raised to −10° C. to get a clear solution and agitated for 90 minutes and then cooled to −60° C.

D) Acylation:

The pre-cooled reactive derivative of step (c) was added to pre-cooled silylated 7-amino-3-(1-pyridiniummethyl)-3-cephem-4-carboxylic acid and the temperature of the reaction mass was kept at −70° C. for 90 minutes. The reaction was monitored by HPLC which showed 70% formation of the product. To the reaction mixture 40 ml of water was added and the aqueous layer was separated. The pH of the aqueous layer was adjusted to 5.2 by adding 8% sodium hydroxide solution. The reaction mixture was cooled to 5° C., stirred for 3–4 hours, and the resulting product obtained was filtered, washed with chilled water (20 ml) and dried in vacuum to obtain 9.5 g (64%) of ceftazidime tert butyl ester.

MP: 138° C. –140° C. IR(KBr) cm$^{-1}$: 3400, 1780, 1720, 1610, 1530. UV (0.N H$_2$SO$_4$): max=256 nm NMR[DMSO-d$_6$], δ(ppm): 1.4(S,9H), 1.55(S,6H),3.6(AB,2H), 5.3(d,1H), 5.6(S,2H),5.92(d,1H), 6.98(S,1 H),8.1–9.1 (5H, pyridinium). Specific Rotation: $[\alpha]_D^{20}$=−31 (C=1% in DMSO).

IV. Preparation of ceftazidime dihydrochloride.

Ceftazidime tert butyl ester (10 g, 16.6 mmol) was dissolved in a mixture of trifluroacetic acid (40 ml) at 15° C. and the resulting solution was stirred for 6 hours at the same temperature followed by addition of water (3 ml) and acetone (180 ml) at 30° C. The reaction mixture was heated to 45° C. and a mixture of HCl and acetone (40:40) was added to it over a period of 90 minutes to get a thick precipitate. The reaction mixture was cooled to 0° C. and stirred for 2 hours. The resulting product was washed with chilled acetone, filtered, dried in vacuum to obtain 3.8 g of ceftazidime dihydrochloride.

MP: 165° C. –168° C. UV(0.1N H$_2$SO$_4$): max=256 nm IR(KBr) cm$^{-1}$: 3500 –2900, 1780, 1720. NMR[DMSO-d$_6$], δ(ppm): 1.45(S,6H), 5.26(d, 1H), 5.84(d,1H), 6.92(S,1H), 8–9.1 (pyridinium). Specific Rotation: $[\alpha]_D^{20}$=−14.2 (C=0.95% in pH 6 buffer) Chlorine content =9.8 –10% Water Content (KF) —4.5 –5%.

V. Preparation of ceftazidime pentahydrate.

A. Crude Ceftazidime Pentahydrate.

Ceftazidime dihydrochloride (8 g, 12.9 mmol) was dissolved in water (35 ml). The resulting solution was cooled to 15° C. and agitated for 30 minutes. The pH of the resulting solution was adjusted to 4.2 by using Amberlite LA-2 solution and agitated for 18 hours at 0° C. to 5° C. The product obtained was filtered, washed with chilled ethyl acetate (12×2 ml) followed by chilled acetone (12 ml), and dried under vacuum at 40° C. to obtain 6.75 g of crude ceftazidime pentahydrate.

Specific Rotation: $[\alpha]_D^{20}$=+24.2 (C-1% in DMSO)

B. Purification of crude ceftazidime pentahydrate

The crude ceftazidime pentahydrate (5 g, 9 mmol) was dissolved in water (10 ml) at 10° C. The solution was cooled to 5° C. and the pH was adjusted to 5.8 to 6 by sodium hydroxide solution to get a clear solution. To the clear solution 0.1 g carbon was added and filtered. The carbon bed was washed with water (2×2 ml). The filtrate and the washings were combined and the pH of the solution was adjusted to 4.4 at 10° C. by using 85% formic acid. The solution was seeded, agitated for 2 hours at 10° C. The reaction mass was cooled to 0° C. and further agitated for another 15 hours. The pH of the reaction mixture was adjusted to 4.2 by using formic acid and further agitated for another 2 hours at 0° C. The resulting product was filtered, washed with chilled water (10 ml) followed by chilled acetone (10 ml) and dried in vacuum to obtain 3.8 g of pure ceftazidime pentahydrate.

MP =135° C. –138° C.

UV (0.1N H$_2$SO$_4$): max =256.4 nm IR (KBr) in cm$_{-1}$: 3500 –3000, 1760, 1720, 1540, 1490, 1160, 680. NMR[250 MHz; DMSO-d$_6$-D$_2$O]δ(ppm): 7.25(S,2H),6.6(S,1H), 5.7(d, 2H),5.65(d,1H), 5.2(d,1 H), 5.05(d,1H), 3.5(d,1 H),3.05(d, 1H), 1.38(S,6H),9.3, 8.6, 8.15(pyridinium). Specific Rotation: $[\alpha]_D^{20}$=+25 (C=1% DMSO).

Example 2

I. Preparation of (6R, 7R)-3-acetoxymethyl-7-[2-(2-amino-thiazol-4-yl)-(Z)-2-[2-tertbutoxycarbonyl-1-methylethoxy) imino]acetamido]-3-cephem-4-carboxylic acid.

A. Silylation of 7-amino cephalosporanic acid (7-ACA)

7-ACA (10 g, 36 mmol) was taken in dichloromethane (60 ml) and hexamethyldisilazane (5.35 g, 33 mmol) was added to it. The reaction mixture was refluxed with stirring for 4 hours to get a clear solution. After cooling the resulting reaction mixture to −40° C., N,N-dimethylaniline (5.25 g, 42 mmol) was added to it and further cooled to −60° C.

B. Preparation of dimethyl formiminium chloride chlorosulfate (DFCCS).

Sulfuryl chloride (6.4 g, 47 mmol) was taken in dichloromethane (60 ml) and the reaction mixture was cooled to −25° C. N,N-dimethylformamide (3.5 g, 47 mmol) was added to the reaction mixture slowly in 30 minutes. The temperature of the reaction mixture was slowly raised to 22° C. at which a very viscous oily layer separates out which was stirred for 90 minutes at 22° C. Further an additional 10 ml of dichloromethane was added to it and stirred for another 15 minutes. The oily layer containing DFCCS was separated out.

C. Activation of (Z)-2-(2-aminothiazol-4-yl)-2-[(1-tertbutoxycarbonyl methylethoxy)imino]acetic acid. (Z)-2-(2-aminothiazol-4-yl)-2-[(1-tertbutoxycarbonyl-1-methylethoxy)imino]acetic acid (12 g, 36 mmol) was taken in dichloromethane (60 ml) and the resulting reaction mixture was cooled to −24° C. The above oily layer of DFCCS was added to it in 30 minutes at −25° C. The temperature of the reaction mixture was raised to −10° C. and stirred for 90 minutes to get a clear solution. This reaction mixture was cooled to −60° C.

D) Acylation:

The pre-cooled reactive derivative of step C was added to pre-cooled silylated 7-ACA at −60° C. The temperature of the reaction mixture was raised to −50° C. to −45° C. The reaction when monitored by HPLC showed 90% formation of the product.

E. Hydrolysis:

To the reaction mass of step D, demineralised water (40 ml) and trimethylamine (25 ml) was added and the temperature was raised to 20° C. The organic and the aqueous layers were separated. The aqueous layer was extracted with dichloromethane (20×2 ml). The organic layer was then combined and dichloromethane was removed by vacuum distillation when a sticky mass was obtained. Water (300 ml) was added to the sticky mass and the pH of the reaction mass was adjusted to 2.8 to 3.0 by conc. HCI. The resulting reaction mixture was cooled to 0° C. and stirred for 3–4 hours. The product obtained was filtered washed with chilled diisopropyl ether (20 ml), dried in vacuum for 2 hours to obtain 16 g (75 –80%) of the title compound having purity of 98%.

MP=152° C.–160° C. IR (KBr) in $cm_{-1}$: 3450, 3350, 1760, 1735, 1710, NMR[DMSO-$d_6$]δ(ppm): 1.38(S,9H), 1.45(S,6H),2.1(S,3H) 4.6(d,1H),5.0(d,1H),5.2(d,1H) 5.8(d, 1H),6.75(S,1H),7.35(S,2H) 9.4(d, 1H)

II. Preparation of (6R, 7R)-7-[(Z)-2-amino-thiazol-4-yl)-2-[(2-carboxy-methylethoxy)imino]acetamido-3-acetoxymethyl-3-cephem-4-carboxylic acid.

The compound of step I (5 g) was treated with trifluoroacetic acid (20 ml) and water (2 ml), and agitated for 3–4 hours at 15° C. After 4 hours 95% of the hydrolysed product was obtained as monitored by HPLC. The reaction mass was added to diisopropyl ether (250 ml) when trifluoroacetic acid salt of the title compound was obtained. Diisopropyl ether was decanted and the white solid obtained was dissolved in water (10 ml). The pH of the resulting solution was adjusted to 7.0 by 12% ammonia solution. The pH was readjusted to 2.8 by 85% formic acid. The reaction mixture was cooled to 5° C. under stirring and the resulting product was filtered, washed with chilled water (10 ml) to obtain 3.5 g of the title compound.

MP =172° C. −176° C. (Decomposes)

MP = 172° C – 176° C. (Decomposes)

1%
UV mass (pH 6.0 buffer): 236 nm ($E_{1cm}$ 250),

1%     1%
inf 255 nm($E_{1cm}$ 238), 296 nm($E_{1cm}$ 103)

Specific Rotation: $[\alpha]_D^{20}$ = +20 (C = 1% DMSO)

Specific Rotation: $[\alpha]_D^{20}$=+20 (C=1% DMSO)

III. Preparation of ceftazidime Pentahydrate

Sodium iodide (7.129 g, 47 mmol) was dissolved in water (3 ml) at 60° C. To the resulting solution, pyridine (3.69 g, 45 mmol) was added followed by the compound of step 11 (2.9 g, 4 mmol). The reaction mixture was agitated for 1 hour at 80° C. and 44% of the product was formed as observed by HPLC. The reaction mixture was cooled and diluted with water (25 ml). The pH of the resulting reaction mixture was adjusted to 6 by using 2N sodium hydroxide. The aqueous layer was extracted with ethyl acetate (2×20 ml). A few drops of the methyl isobutyl ketone was added to it. The pH of the solution was further adjusted to I by conc. HCl. The separated solid was filtered and the pH of the collected filtrate was slowly adjusted to 3.8 to 4.0 by using Amberlit LA-2 in 30 minutes and stirred for 15 hours at 0° C. to 5° C. The product obtained was filtered, washed with small amount of ethyl acetate and acetone, and dried under vacuum to obtain 0.23 g of the title compound.

MP=135° C. −138° C. UV (0.1N $H_2SO_4$): max=256.4 nm IR (KBr) in $cm_{-1}$: 3500 −3000, 1760, 1720, 1540, 1490, 1160, 680 NMR[250 MHz, DMSO-$d_6$-$D_2O$]δ(ppm): 7.25(S, 2H),6.6(S,1H), 5.7(d,2H),5.65(d,1H),5.2(d,1H), 5.05(d,1H) ,3.5(d,1H),3.05(d,1H), 1.38(S,6H),9.3,8.6,8.15(pyridinium) Specific Rotation: $[\alpha]_D^{20}$=+25 (C=1% DMSO)

We claim:

1. The compound of formula I

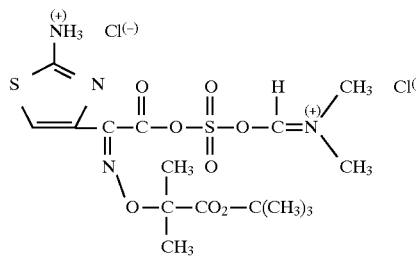

2. A process for the production of compound of formula I

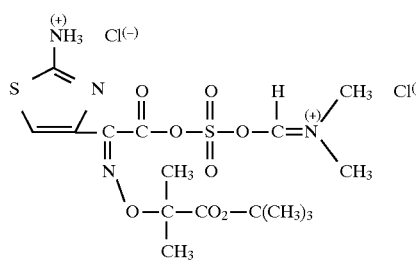

comprising:

reacting dimethyl formiminium chloride chloro sulphate (DFCCS) of formula (IX):

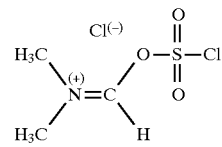

with (Z)-2-(2-aminothiazol-4-yl)-2-[(1-tertbutoxycarbonyl-1-methylethoxy)imino]acetic acid (VIII) in a solvent at a temperature ranging from −20° C. to −25° C.

3. A process as claimed in claim 2, wherein the temperature is about −20° C.

4. A process as claimed in claim 2, wherein said solvent used is selected from dichloromethane, chloroform, benzene and toluene.

5. A process as claimed in claim 2, wherein said DFCCS of formula (IX) is N,N-dimethyl formiminium chloride chlorosulphate obtained by reacting dimethyl formamide (DMF) with sulfuryl chloride.

6. A process as claimed in claim 2, wherein the molar ratio of the DFCCS (IX) to the (Z)-2-(2-aminothiazol-4-yl)-2-acetic acid (VIII) is 1.0 to 1.3.

7. A process for the preparation of ceftazidime of formula II,

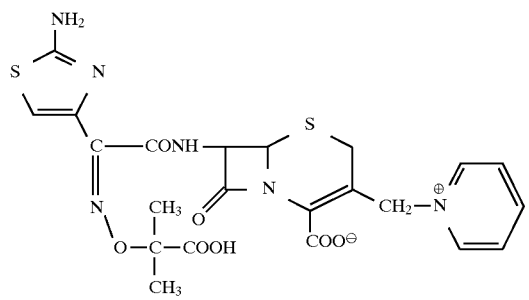

which comprises:

a) silylating 7-amino-3-(1-pyridiniummethyl)-3-cephem-4-carboxylic acid of formula III

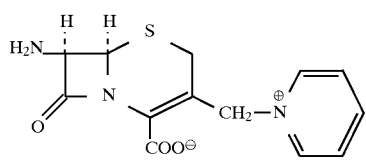

with a silylating agent in the presence of an acid scavenging agent at a temperature ranging from 18° C. to 25° C. to provide silylated 7-amino-3-(1-pyridiniummethyl)-3-cephem-4-carboxylic acid of formula (X);

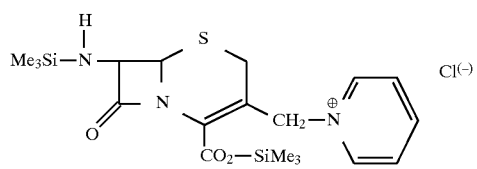

b) activating (Z)-2-(2-aminothiazol-4-yl)-2-[(1-tertbutoxycarbonyl-1methylethoxy)imino]acetic acid (VIII)

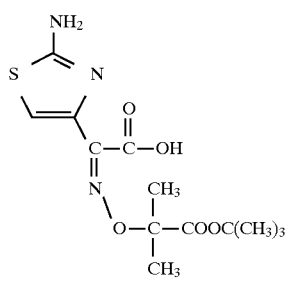

with N,N-dimethylformiminium chloride chlorosulfate (DFCCS) (IX)

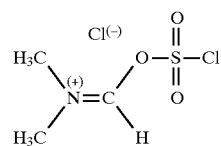

in dichloromethane at a temperature ranging from −20° C. to −25° C. to provide a compound of formula I:

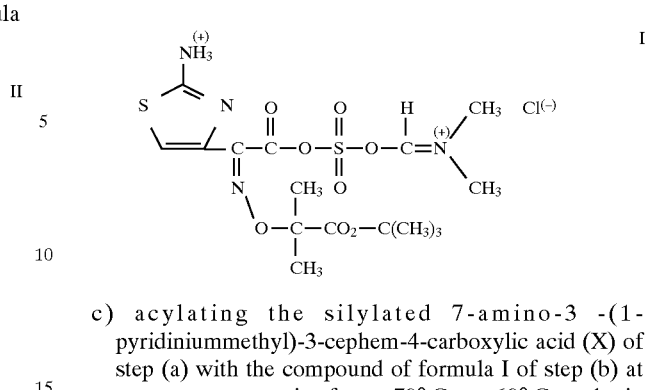

c) acylating the silylated 7-amino-3-(1-pyridiniummethyl)-3-cephem-4-carboxylic acid (X) of step (a) with the compound of formula I of step (b) at a temperature ranging from −70° C. to −60° C. to obtain ceftazidime tertbutyl ester (VI),

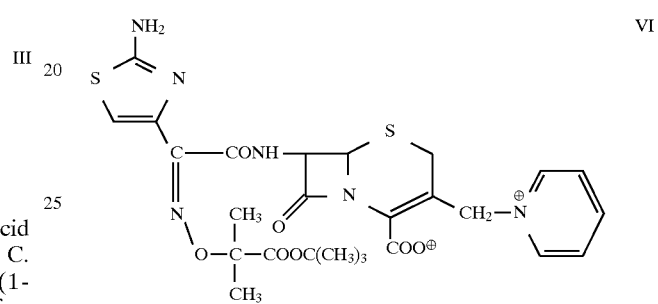

and (d) hydrolyzing the ceftazidine tert-butyl ester to obtain the ceftazidine of formula II.

8. A process as claimed in claim 7, wherein the temperature in step (c) is from −70° C. to −65° C.

9. A process as claimed in claim 7 wherein the silylated 7-amino-3-(1-pyridiniummethyl)-3-cephem-4-carboxylic acid (X) is reacted with said reactive derivative of formula I in the presence of an acid scavenging agent.

10. A process as claimed in claim 9, wherein the said acid scavenging agent is selected from N,N-dimethylaniline, diethylamine, and pyridine.

11. A process as claimed in claim 10, wherein the acid scavenging agent is N,N-dimethylaniline.

12. A process as claimed in claim 7, wherein the silylating agent is selected from N,O-bis(trimethylsilyl)acetamide, hexamethyldisilazane, trimethyl chlorosilane.

13. A processes claimed in claim 12, wherein the silylating agent is N,Obis(trimethylsilyl)acetamide.

14. A process as claimed in claim 7, wherein the molar ratio of DFCCS (IX) to (Z)-2-(2-aminothiazol-4-yl)-2-[(1-tertbutoxycarbonyl-1-methylethoxy)imino]acetic acid (VIII) is 1.0 to 1.3.

15. A process as claimed in claim 7, wherein said acylation reaction is carried out by maintaining pH of the reaction mixture at 4.5 to 7.5.

16. A process as claimed in claim 7, wherein said DFCCS of formula IX is prepared by reacting dimethyl formamide (DMF) with sulfuryl chloride.

17. A process as claimed in claim 16, wherein said DFCCS of formula IX is prepared by reacting equimolar amounts of sulfuryl chloride and dimethyl formamide.

* * * * *